(12) United States Patent
Dyshlyuk et al.

(10) Patent No.: US 9,612,167 B2
(45) Date of Patent: Apr. 4, 2017

(54) METHOD FOR DETERMINING ADSORPTION HEAT AND WETTING HEAT OF A SURFACE AND A MEASURING CELL OF A CALORIMETER

(71) Applicant: SCHLUMBERGER TECHNOLOGY CORPORATION, Sugar Land, TX (US)

(72) Inventors: Evgeny Nikolaevich Dyshlyuk, Moscow (RU); Vitaly Alekseevich Baldygin, Istra (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 499 days.

(21) Appl. No.: 14/109,688

(22) Filed: Dec. 17, 2013

(65) Prior Publication Data

US 2014/0177669 A1 Jun. 26, 2014

(30) Foreign Application Priority Data

Dec. 24, 2012 (RU) ................................ 2012155807

(51) Int. Cl.
  *G01K 17/02* (2006.01)
  *G01K 17/00* (2006.01)
  *G01N 25/48* (2006.01)

(52) U.S. Cl.
  CPC ............ *G01K 17/00* (2013.01); *G01K 17/02* (2013.01); *G01N 25/4846* (2013.01); *G01N 25/4853* (2013.01)

(58) Field of Classification Search
  CPC ...................................................... G01K 17/02
  See application file for complete search history.

(56) References Cited

U.S. PATENT DOCUMENTS 6,444,001 B1 * 9/2002 Sheffield ............... B01D 45/02
  55/319
7,952,698 B2 5/2011 Friedrich et al.

FOREIGN PATENT DOCUMENTS

DE      111466 A1   2/1975
JP    2003075382 A  3/2003

OTHER PUBLICATIONS

"Database WPI", Week 200327, Thomson Scientific, London, GB; AN 2003-272380, XP002723308, 2 pages.
Broadbent, "The surface area of graphite calculated from adsorption isotherms and heats of wetting experiments", Carbon, vol. 4, No.(2), Jul. 1, 1966, pp. 281-287.

(Continued)

*Primary Examiner* — Paul West

(57) ABSTRACT

A sample of a material is placed into a measuring cell of a calorimeter consisting of upper and the lower parts connected with each other by a movable detachable tight connection. The cell is equipped with two coaxially arranged tubes capable of independent connection to external devices. An outer tube is connected to the upper part of the cell and an inner tube is connected to the lower part of the cell via the movable detachable tight connection and is movable. At least once a contact of the sample with vapor of a liquid is provided and heat of adsorption is measured, then contact of the sample with the same or another liquid is provided and heat of wetting of the sample by the same or the other liquid is measured.

7 Claims, 4 Drawing Sheets

(56) References Cited

OTHER PUBLICATIONS

Maggs, et al., "A recording calorimeter for the rapid determination of heats of wetting", Journal of Scientific Instruments, vol. 39, No. 7, Jul. 1, 1962, pp. 364-366.
Tarasevich, et al., "Microcalorimetric Study of Water Adsorption on Initial and Polyfluoroalkylated Silicas", Colloid Journal, vol. 67, No. 5, Sep. 1, 2005, pp. 638-643.
Amott, "Observations Relating to the Wettability of Porous Rock," Petroleum Transactions, 1959, vol. 216: pp. 156-162.
Aukett, "A New Membrane Cell for the Determination of Heats of Immersion Using the Setaram C-80 Microcalorimeter," Journal of Thermal Analysis, 1988, vol. 33: pp. 323-327.
Bozhko, "Detachable tight connections (Split Hermetical Compounds)," Transactions TSTU, 2010, vol. 16(2): 404-420 (English Abstract on p. 419).
Denoyel et al., "Thermodynamics of wetting: information brought by microcalorimetry," Journal of Petroleum Science and Engineering, 2004, vol. 45: pp. 203-212.
Partyka et al., Calorimetric Determination of Surface Areas: Possibilities of a Modified Harkins and Jura Procedure, Journal of Colloid and Interface Science, Jan. 1979, vol. 68(10): pp. 21-31.
Poledníček et al., "Flow unit for measuring heats of mixing at subambient conditions," Review of Scientific Instruments, 2005, vol. 76: pp. 074102-1-074102-9.
Trantham et al., "SPE 5802: Determination of Oil Saturation After Waterflooding in an Oil-Wet Reservoir—The North Burbank Unit, Tract 97 Project," Journal of Petroleum Technology, May 1977: pp. 491-500.

\* cited by examiner

METHOD FOR DETERMINING ADSORPTION HEAT AND WETTING HEAT OF A SURFACE AND A MEASURING CELL OF A CALORIMETER

CROSS-REFERENCE TO RELATED REFERENCE

This application claims priority to Russian Application No. RU2012155807 filed Dec. 24, 2012, which is incorporated herein by reference in its entirety.

FIELD OF THE INVENTION

The invention relates to the field of studying properties of interaction of a surface with fluids (liquid, gas/vapor), in particular, to studying adsorption and wetting heats of a surface and may be used in different industries, for example in oil and gas, paint and varnish and food industries.

Heat or quantity of heat is a measure of energy transferred from one body to another in the process of heat transfer. Heats of various physicochemical processes can be measured with the use of calorimeters of various types, such as, for example, as a differential scanning calorimeter (DSC).

Adsorption is a process of change in concentration of a substance near a surface. Heat of adsorption is an energy that is released or absorbed in the form of heat in the process of adsorption. Heat of wetting is an energy that is released or absorbed in the form of heat in the process of wetting of a sample with a liquid, i.e., in the process in which a surface that was initially in contact with vacuum is entirely immersed in a liquid, in such a way that the entire accessible surface of the sample remains covered with the said liquid.

Measurements of adsorption and/or wetting heat make it possible to obtain additional information about structure of surface of a sample (for example, to estimate a surface area of the sample) or about the character of interaction of the sample surface with gases and liquids taking part in the processes of adsorption and wetting (for example, the character of wetting of the surface—wettability).

Wettability is capability of a liquid to spread over a surface of a solid body, to remain in contact with it or lose contact with this surface in the presence of another liquid that is immiscible with the first one. Wettability is one of the most important parameters characterizing interaction of two immiscible liquids with surface of a solid body in oil and gas industry, pharmaceutics and in other industries.

For example, in oil and gas industry, wettability is one of the key parameters determining position of fluids in a pore space of a hydrocarbon deposit, as well as distribution of fluid flows. Being a key parameter determining position of fluids in the pore space, wettability of a rock exerts influence on all types of measurements of formation parameters—electric properties, capillary pressure, relative phase permeabilities, etc. Wettability affects methods and effectiveness of oil production, especially in the process of secondary and tertiary methods of oil recovery.

BACKGROUND OF THE INVENTION

The main method for estimating wettability of a solid surface with two immiscible liquids is the method of studying a contact angle formed by phase interface with the solid surface (see, for example, U.S. Pat. No. 7,952,698).

The main disadvantages of the known method are a long time needed for achieving the equilibrium contact angle (up to 1000 hours), contact angle hysteresis caused by different reasons such as heterogeneous structure of the surface, surface irregularities, etc. Another serious disadvantage of this method is that the said method can be applied to smooth flat surfaces only and adaptation of this method to measurement in porous media is rather difficult and in some case is impossible at all. For example, in oil and gas industry, rather than the method of contact angle study, petrophysical investigations of rock core samples are used for determining wettability of porous media. It is in a small number of cases, with a pronounced character of wettability, that wettability can be estimated by results of other methods of investigations. In petrophysical investigations of rock cores, the Amott's method is mainly used (E. Amott, "Observations Relating to the Wettability of Porous Media," Trans, AIME, 216, 156-162, 1959) or its modifications: the Amott-Harvey and USBM methods (see, for example, J. C. Trantham, R. L. Clampitt, "Determination of Oil Saturation After Waterflooding in an Oil-Wet Reservoir—The North Burbank Unit, Tract 97 Project," JPT, 491-500 (1977)).

All of these methods simulate a process of oil production from a reservoir and are based on successive substitution of oil for a mineral solution or a mineral solution for oil through natural or forced (by means of centrifugation) imbibitions of a sample with measurement of saturation with fluids. All of the above-listed methods are indirect methods of investigation and provide no accurate thermodynamic information about such thermodynamic characteristic as wettability. Another disadvantage of these methods is their low sensitivity in the area of neutral wettability or with small dimensions of a sample.

In recent years, the method of wettability determination based on calorimetric measurements of wetting heat is being actively developed. Investigations of wettability in a system solid—liquid—gas (saturated vapor of this fluid) were conducted (see, for example, R. Denoyel, I. Beurroies, B. Lefevre, "Thermodynamics of wetting: information brought by microcalorimetry," J. of Petr. Sci. and Eng., 45, 203-212, 2004). Among advantages of this method, one can mention high accuracy of wettability estimation based on thermodynamic measurements, among disadvantages—a low sensitivity in case of small accessibility of sample surface.

Wetting heat can also be used for determining a surface area of a sample with the use of the modified Harkins-Jura method (Partyka S., Rouquerol F., Rouquerol J. "Calorimetric determination of surface areas: possibilities of a modified Harkins and Jura procedures." Journal of colloid and interface science, Vol. 68, No. 1, January 1979).

For measurement of adsorption heat, various calorimetric cells may be used. Glass or metal cells are most often used. Before an experiment, a surface of a sample is cleaned by means of evacuation under the effect of increased temperature. In the process of examining adsorption heat, vapor of a liquid under examination is supplied into a cell under controlled pressure and after that heat of adsorption is measured.

For measurement of wetting heat, various types of calorimeter measuring cells are used. Most often, a pressure tight cell is used inside which a sample closed in a sealed glass balloon is placed (see, for example, R. Denoyel, I. Beurroies, B. Lefevre, "Thermodynamics of wetting: information brought by microcalorimetry," J. of Petr. Sci. and Eng., 45, 203-212, 2004). The balloon with the sample is previously evacuated and sealed off, that making it possible to obtained a controllable state of sample surface before the experiment. When conducting the experiment, the balloon is broken and the sample is wetted with the liquid. A membrane cell is a cell divided by a membrane, as a rule made of metal, into two parts. The sample is placed into a lower part and the liquid—into an upper one. In the process of experiment, the membrane is cut and the liquid flows into the lower part of the cell. The advantage of this type of cell is that in this case no sealing of the sample in a glass balloon is needed; the disadvantage is that the sample in this case is not evacuated, which may result in serious measurement errors for wetting heat. In yet another version, a cell merges advantages of the two above-described designs (see, for example, P. N. Aukett "A new membrane cell for the determination of heats of immersion using the Setaram c-80 microcalorimeter" Journal of Thermal Analysis, Vol. 33, 323-327, 1988). The liquid and the sample are separated by a membrane, while the lower part of the cell has a vacuum lock and can be evacuated before the experiment. The disadvantage of all of the above-mentioned cells is impossibility to control pressure during the experiment because the cells are not connected with other parts of the setup by means of tube connections. In such cells, it is difficult, if not impossible, to conduct experiments under increased pressures.

In the work (R. Denoyel, I. Beurroies, B. Lefevre, "Thermodynamics of wetting: information brought by microcalorimetry," J. of Petr. Sci. and Eng., 45, 203-212, 2004), it is proposed to utilize for measurement of wetting heat an apparatus in which pressure in a cell can be controlled. The measuring cell, via tubular connections, is connected via a T-adapter with a vacuum pump on the one side, which makes it possible to evacuate the sample before the experiment, and on the other side with a system that makes it possible to supply the liquid to the cell and to create pressure of this liquid in the cell. It should be noted that the liquid supplied into the cell should have a temperature close to the temperature in the measuring system in order not to create an additional heat flow rendering difficult the wetting heat measurement.

For each of the proposed configurations, it is necessary to account for additional thermal effects appearing in the process of experiment that are connected with breaking a balloon or rupture of a membrane, a thermal effect appearing as a result of temperature difference between the liquid entering into the cell and temperature of the cell, thermal effect associated with compressing of the liquid in the cell (when increasing pressure to the required level), etc. These thermal effects, as a rule, can be accounted for through conducting additional measurements.

SUMMARY OF THE INVENTION

The invention provides an enhanced quality and effectiveness of measurement of adsorption and wetting heat at various pressures and temperatures, increased rate of these measurements and at the same time reduces a risk of conducting these measurements incorrectly.

A sample of a material is placed into a measuring cell of a calorimeter and at least once a contact of the sample with vapor of a liquid under controlled vapor pressure is provided. A heat of adsorption is measured. After that contact of the sample with the same or another liquid is provided and a wetting heat of the sample surface with the same or the other liquid is measured.

In accordance with one embodiment of the invention, after measuring the adsorption heat the sample is evacuated and a desorption heat is measured. The adsorption-desorption cycle may be repeated.

In accordance with another embodiment of the invention, after measuring the adsorption of the liquid, the sample is brought in contact with vapor of a second liquid and an adsorption heat of the second liquid is measured.

The sample may be preliminary dried, purified and evacuated.

The cell with the sample is preferably kept until stabilization of heat a flow, at the temperature at which the adsorption heat and the wetting heat are measured.

A rock core may be used as the sample.

Any liquids may be used as liquids for adsorption and wetting, both same and different, in particular water and water, water and oil, or water and salt solution, salt solution and oil, at formation pressures and temperatures including.

To measure adsorption and wetting heats, a measuring cell of a calorimeter may be used comprising two isolated parts—an upper part and a lower part, which are connected with each other by a movable detachable tight connection. The cell is equipped with two coaxially arranged tubes capable to be independently connected to external devices, an outer tube is connected to the upper part of the cell and an inner tube is connected to the lower part of the cell via the movable detachable tight connection and is movable.

The external devices to which the upper and the lower parts of the cell may be connected independently of each other are a device for evacuation, a device for feeding a wetting liquid and a vapor, and a device for maintaining pressure in the cell.

The inner tube may be movable in vertical direction. Pressure-sealing of the movable detachable tight connection may be provided by connection of two surfaces, for example cone-cone, sphere-cone or plain surface—plain surface.

The inner tube may be rotatable around its axis, and pressure-sealing of the movable detachable tight connection may be provided by closing a passageway of the tube, for example a ball valve.

BRIEF DESCRIPTION OF THE DRAWINGS

The invention is explained by drawings where.

DETAILED DESCRIPTION OF THE PREFERRED EMBODIMENTS

A sample of a material is placed into a cell of a differential scanning calorimeter (DSC). A surface of the sample may be previously purified. For example, in oil industry a rock sample as a rule is extracted and then evacuated at increased temperatures in a vacuum oven. Temperature and duration of sample drying are selected proceeding from properties of a particular sample being studied. In particular, for rock samples, drying in vacuum at an increased temperature (~100° C.) for a rather long period of time is used for removal of moisture—about 24 hours. Accelerated drying at higher temperatures is possible if temperature increase does not result in structural changes of the sample surface.

DSCs are capable of operating at various temperatures (temperature range depends on a model of a calorimeter), some DSCs may be equipped with cells allowing measurements at increased pressures or in vacuum. For conducting measurements described in this invention, a DSC should be combined with a system capable of creating controllable pressure in calorimeter cells. Such a system makes it possible to control pressure in the cells in the process of experiment, making it possible to conduct measurements of adsorption and wetting heats with a better quality, at increased pressures including. As such a system, pumps of different types may be used, in a combination with pressure sensors and connected to the calorimeter cells by means of tubular connections.

The sample is placed into the calorimeter cell and is evacuated. Purifying of the sample and evacuation can be combined because construction of the proposed calorimeter cell makes it possible to evacuate the sample at increased temperatures directly in the calorimeter cell. The sample is not evacuated if evacuation does not affect the final result of experiment—adsorption and wetting heats.

The cell is kept until stabilization of a heat flow at a temperature at which the measurements will be conducted Liquids to be used for measuring adsorption and wetting heats are prepared, the liquids should be purified from impurities and evacuated for removal of dissolved gases.

Figure 1:
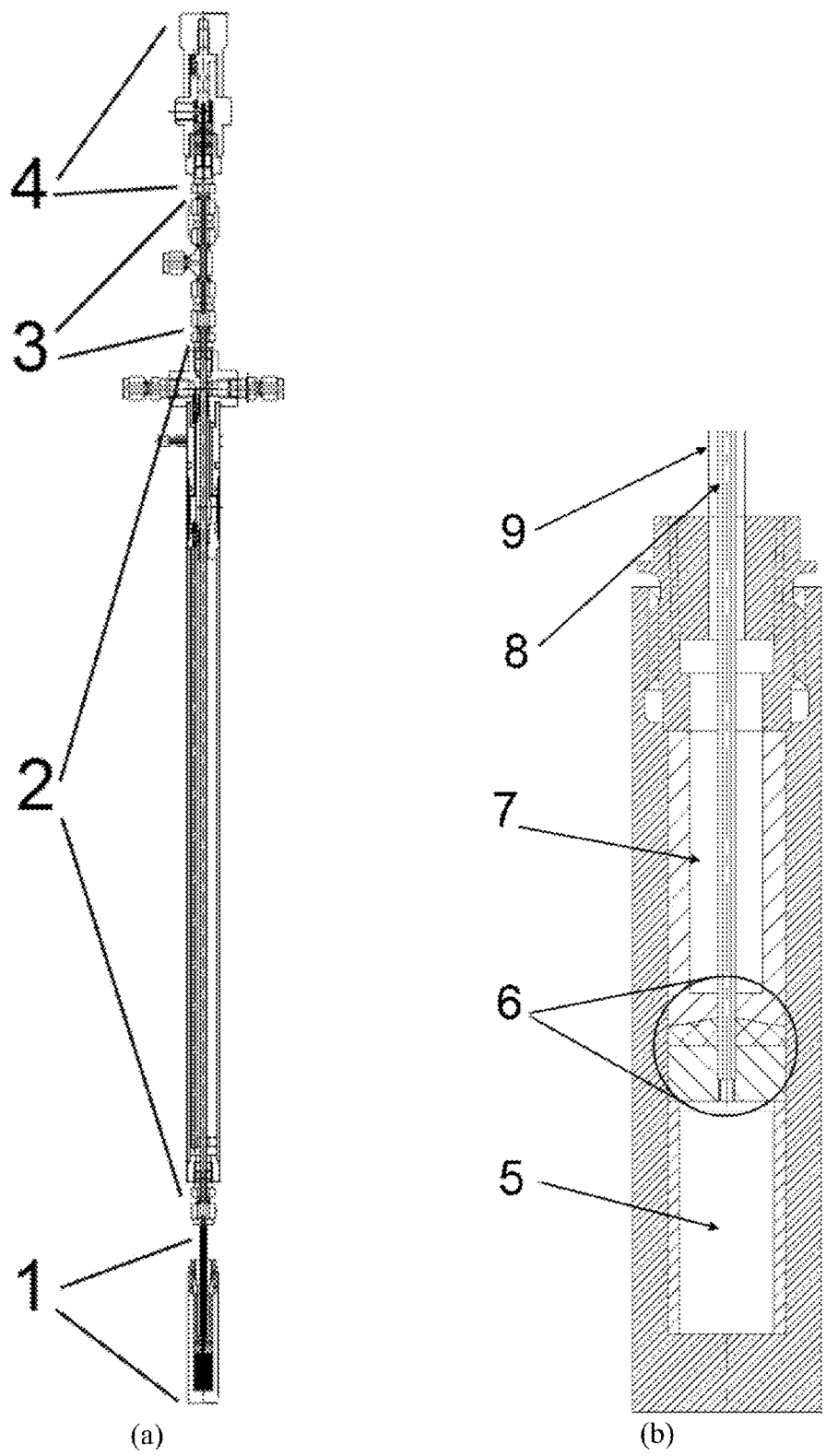
FIG. 1(a) shows a scheme of the device for measuring an adsorption heat and a wetting heat.
FIG. 1(b) shows a measuring cell of a calorimeter.

FIG. 1(a) shows a scheme of the device for determining adsorption and wetting heats wherein: 1—a measuring cell, 2—a heater, 3—connections of feeding tubes for independent connection of upper and lower parts of the measuring cell to external devices, 4—a device providing connection/ disconnection of the lower and upper parts of the measuring cell by means of translational, rotational or translational-rotational movement of an inner coaxial tube.

FIG. 1(b) shows the calorimeter cell consisting of the lower part 5 in which the sample is placed and the upper part 7. The upper and the lower parts are isolated and are connected between themselves by the movable detachable tight connection 6. The upper part 7 of the cell, by an outer tube 9 of the coaxial connection, may be connected to external devices such as a device for feeding a liquid and a device for maintaining pressure in the cell. Independently of the upper part 7 of the cell, the lower part 5 of the cell, by means of the inner tube 8 of the coaxial connection also may be connected to external devices such as a vacuum pipe and a device for feeding vapor. The inner tube 8 is connected to the lower part 5 of the cell via the movable detachable tight connection 6, which, during movement of the inner tube 8 up and down or during its rotation, provides connection of the upper and lower parts of the cell between each other.

Figure 2:
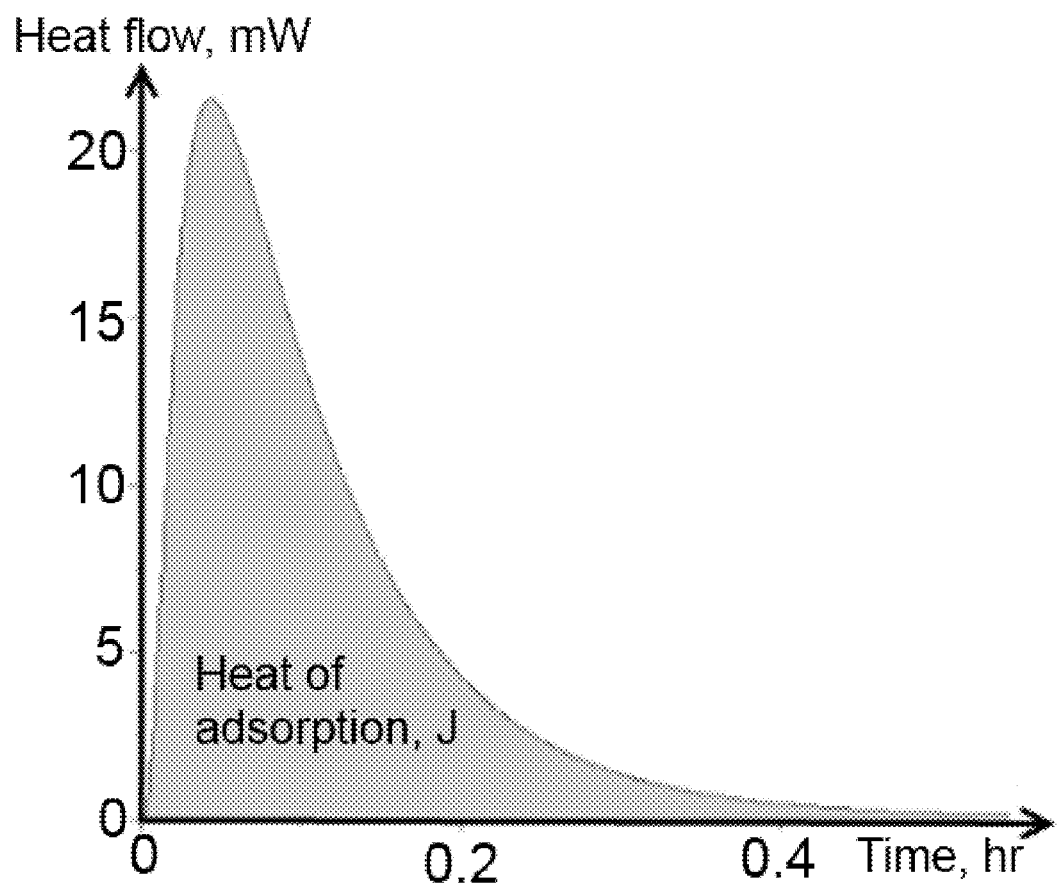
FIG. 2 shows a diagram of adsorption heat measurement.
Figure 3:
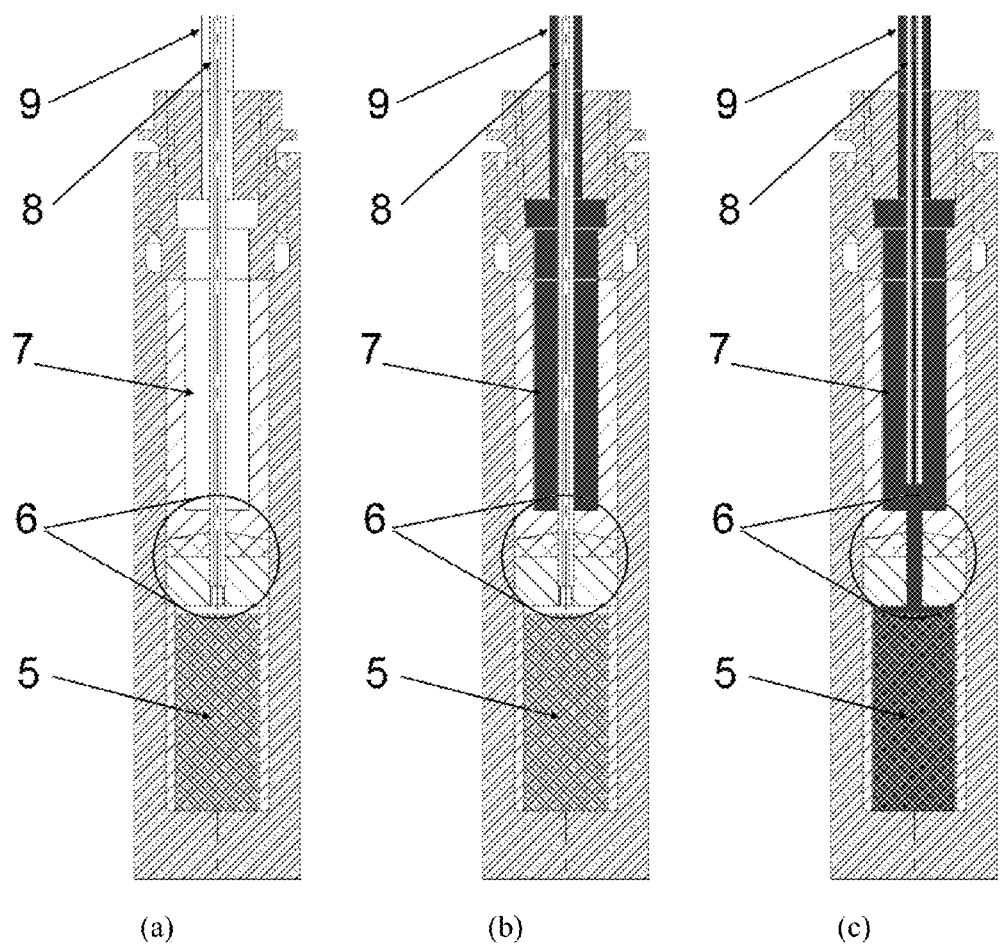
FIG. 3 shows a scheme of operation of the calorimeter cell.

FIG. 3 shows the scheme of operation of the proposed calorimeter cell. As is shown in FIG. 3(a), before starting the experiment the sample is placed in the lower part 5 of the cell and is evacuated by means of, for example, a vacuum pump connected to the lower part 5 of the cell via the inner tube 8. Into the upper part 7 of the cell, by means of the outer tube 9, a liquid to be used for wetting of the sample is delivered (see FIG. 3(b)). For studying an adsorption heat, vapor of the liquid is delivered through the inner tube 8 to the lower part 5 of the cell; the lower part 5 of the cell also may be evacuated afterwards to study a desorption heat. For measuring the adsorption heat, a measured electric signal from calorimeter sensors is translated into a heat flow (for this, calibration of the calorimeter is preliminary made); summation of the heat flow in time after deduction of a baseline makes it possible to determine the adsorption heat. FIG. 2 shows a relationship of the heat flow versus time measured in the process of adsorption, summation of the heat flow versus time after deduction of the baseline (the value of heat flow before start of the experiment)—the fill area is the heat of adsorption.

To measure a heat of wetting, the lower part 5 of the cell must be connected with the upper part 7 by means of movement of the inner tube 8 (see FIG. 3(c)). This movement may be a movement up and down or rotation about its axis. The liquid contained in the upper part 7 of the cell, due to pressure difference in these parts and/or force of gravity, gets to the lower part 5 of the cell where it wets the sample. The liquid removed from the upper part 7 of the cell is substituted for liquid or gas contained in the outer part of the tube 9 connecting the upper part 7 of the cell with other parts of the device. It is necessary for the liquid displacing the liquid from the upper part 7 of the cell to be in good match in temperature with the liquid contained in the cell itself. To change a temperature of this liquid, an electric heater with a temperature sensor may be used (see, for example, M. Polednicek, V. Majer, V. Hynek, J. Jose, "Flow unit for measuring heats of mixing at subambient conditions," Review of Scientific Instruments 76, 074102, 2005) or a liquid circulation heater/cooler with a temperature sensor (see FIG. 1).

Figure 4:
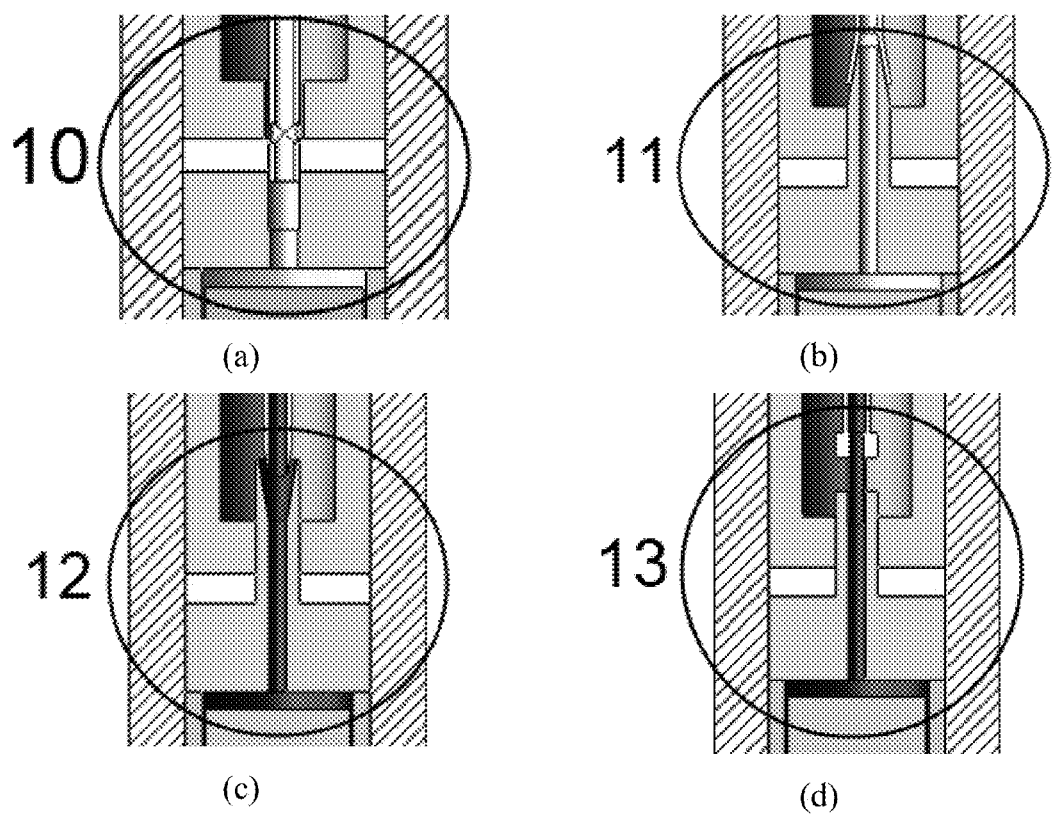
FIG. 4 shows different types of movable detachable tight connections that may be used for connecting an inner tube of a coaxial connection with a lower part of the calorimeter cell.

Connection of the two parts of the cell is made by means of movement of the inner tube 8. For connecting/disconnecting the two parts of the cell, it is possible to use a movable detachable tight connection of different types, in particular it is possible to use: a connection with a seal of the inserted tube through a gasket 10 made of a soft material (FIG. 4a), a cone-over-cone connection 11, or a sphere-over-cone connection 12 (FIG. 4b, c), a connection with a flat seal 13 made of metal or a softer material (FIG. 4d) (see, for example, "Detachable tight connections" G. V. Bozhko, ISSN 0136-5835, Vestnik TGTU, 2010, Vol. 16. No 2. Transactions TSTU).

Wetting heat is determined similar to the adsorption heat. The measured electric signal from the calorimeter sensors is translated into a heat flow, summation of the heat flow in time with deduction of the baseline in the process of conducting the experiment makes it possible to determine the heat of wetting.

Additional thermal effects not associated with the effects of adsorption and wetting are also taken into account.

The invention claimed is:

1. A measuring cell of a calorimeter comprising:
an upper part and a lower part separated from each other and configured to be connected with each other, the lower part of the cell being used for placing a sample,
two coaxially arranged tubes, an outer tube connected to the upper part of the cell for feeding a liquid into the upper part of the cell and for maintaining pressure in the cell, and an inner tube connected to the lower part of the cell for evacuating the cell and feeding vapor of the liquid into the lower part of the cell, the inner tube is movable and is connected to the lower part of the cell through a movable detachable tight connection which during movement of the inner tube provides connection of the lower and the upper parts of the cell between each other.

2. The calorimeter measuring cell of claim 1, wherein the inner tube is movable in vertical direction.

3. The calorimeter measuring cell of claim 1, wherein tightness of the movable detachable tight connection is provided by a junction of two surfaces.

4. The calorimeter measuring cell of claim 1, wherein tightness of the movable detachable tight connection is provided by a cone-to-cone, a sphere-to-cone or a flat surface-to-flat surface junction.

5. The calorimeter measuring cell of claim 1, wherein the inner tube is rotatable around axis of symmetry of the inner tube.

6. The calorimeter measuring cell of claim 1, wherein tightness of the movable detachable tight connection is provided by closing a passageway of the inner tube.

7. The calorimeter measuring cell of claim 6, wherein the movable detachable tight connection is a ball valve.

* * * * *